(12) United States Patent
Iwasaki

(10) Patent No.: US 6,239,295 B1
(45) Date of Patent: May 29, 2001

(54) PROCESS FOR PRODUCING 3-METHYLTETRAHYDROFURAN, AND PROCESS FOR PRODUCING AN INTERMEDIATE THEREOF

(75) Inventor: Hideharu Iwasaki, Kurashiki (JP)

(73) Assignee: Kuraray Co., LTD, Kurashiki (JP)

( * ) Notice: Subject to any disclaimer, the term of this patent is extended or adjusted under 35 U.S.C. 154(b) by 0 days.

(21) Appl. No.: 09/577,318

(22) Filed: May 24, 2000

(30) Foreign Application Priority Data

| May 24, 1999 | (JP) | ................................. | 11-142631 |
| Sep. 22, 1999 | (JP) | ................................. | 11-268274 |
| Dec. 6, 1999 | (JP) | ................................. | 11-346141 |
| Dec. 7, 1999 | (JP) | ................................. | 11-347467 |

(51) Int. Cl.$^7$ ................................. C07D 307/02
(52) U.S. Cl. ................................. 549/506
(58) Field of Search ................................. 549/506

(56) References Cited

U.S. PATENT DOCUMENTS

| 3,932,468 | 1/1976 | Kurkov | ................................. | 261/347.1 |
| 3,956,318 | 5/1976 | Suzuki | ................................. | 260/346.1 R |

FOREIGN PATENT DOCUMENTS

WO 91/13882   9/1991   (WO).

OTHER PUBLICATIONS

Anil Wali, et al., Ind. Eng. Chem. Res., vol. 33, pp. 444–447, "Cyclodehydration of Diols Catalyzed By $CP_xMCl_{4-x}$ (x =0–2; M=Ti, Zr, Hf)", 1994.

Kyoko Takahashi, et al., Bull. Chem. Soc. Jpn., vol. 65, No. 1, pp. 262–266, "Reduction of Dicarboxylic Acid Anhydride With 2–Propanol Over Hydrous Zirconium Oxide", 1992.

C. Botteghi, et al., Journal f. prakt. Chemie, vol. 314, No. 5–6, pp. 840–850, "Synthese Von Optisch Aktiven Und Racemischen 3–Alkyltetrahydrofuranen", 1972.

J.–P. Bats, et al., Tetrahedron, vol. 38, No. 14, pp. 2139–2146, "Transposition Des Oxirannes–Ethanols Par L'Intermediaire D'Alcoxyetains", 1982.

Yves Infarnet, Bulletin de la Société Chimique de France, No. 5–6, pp. 261–266, "Étude Des Transformations Catalytiques Sur Alumine De β–Tétrahydrofuryméthanols", 1980.

Nippon Kagaku Kaishi, pp. 1021–1025, 1977.

T. Miyakoshi, Meiji Daigaku Gijutu Kenkyusho Nempo, vol. 17, p. 22, 1975 (with corr. Chemical Abstract AN 135962g, 1977).

C. Botteghi, et al., J. Org. Chem., vol. 37, No. 11, pp. 1835–1837, "A Convenient Synthetic Approach To 3–And 4–Alkyl–2,3–Dihydrofurans", 1972.

Edward E. Schweizer, et al., The Journal of Organic Chemistry, vol. 33, No. 2, pp. 583–584, "Reactions of Phosphorus Compounds. XIV. A General Synthesis of 2,5–Dihydrofurans", Feb. 1968.

H.M.R. Hoffmann, Angew. Chem. Internat. Edit., vol. 8, No. 8, pp. 556–577, "The Ene Reaction", 1969.

*Primary Examiner*—Alan L. Rotman
*Assistant Examiner*—Raymond Covington
(74) *Attorney, Agent, or Firm*—Oblon, Spivak, McClelland, Maier & Neustadt, P.C.

(57) ABSTRACT

A process for producing 3-methyltetrahydrofuran, and processes for producing 3-hydroxy-3-methyltetrahydrofuran and 3-methyldihydrofuran, which are intermediates thereof, are provided.

25 Claims, No Drawings

PROCESS FOR PRODUCING 3-METHYLTETRAHYDROFURAN, AND PROCESS FOR PRODUCING AN INTERMEDIATE THEREOF

BACKGROUND OF THE INVENTION

1. Field of the Invention

The present invention relates to a process for producing 3-methyltetrahydrofuran, and processes for producing 3-hydroxy-3-methyltetrahydrofuran and 3-methyldihydrofuran, which are intermediates thereof. 3-Methyltetrahydrofuran obtained by the present invention is useful as a starting material of polyether polyol, which is, for example, a component of a thermoplastic polyurethane, or a solvent. 3-Hydroxy-3-methyltetrahydrofuran and 3-methyldihydrofuran obtained by the present invention are useful as starting materials for chemicals such as medicines or agricultural chemicals.

2. Description of the Background

The following conventional processes for producing 3-methyltetrahydrofuran are known: (a) a process of cyclodehydrating 2-methyl-1,4-butanediol [see Ind. Eng. Chem. Res., 33, pp. 444–447 (1994)], (b) a process of hydrogenating methylsuccinic acid, using isopropanol as a hydrogen source, over hydrous zirconium oxide catalyst [see Bull. Chem. Soc. Jpn., 65, pp. 262–266 (1992), (c) a process of hydroformylating methallyl alcohol, hydrogenating the resultant formylated product, and then cyclodehydrating the hydrogenated product [see J. Prakt. Chem., 314, pp. 840–850 (1972)], and (d) a process of hydrogenating 3-methyl-3,4-epoxybutan-1-ol in an acidic aqueous solution [see U.S. Pat. No. 3,956,318].

However, in process (a), it is difficult to obtain 2-methyl-1,4-butanediol industrially, which is a starting material. In process (b), preparing hydrous zirconium oxide catalyst is complicated, and acetone is formed as by-product in an equivalent to the amount of isopropanol used as the hydrogen source. In process (c), a rhodium compound used as a catalyst for the hydroformylation reaction is expensive. Moreover, methallyl alcohol, which is a starting material, is not industrially produced so that it is difficult to obtain the alcohol easily and economically. In process (d), 3-methyl-3,4-epoxybutan-1-ol is not industrially produced so that it is difficult to obtain the compound easily and economically. Besides, under reaction conditions in the acidic aqueous solution, the starting material tends to be hydrolyzed to produce a triol as by-product, which is formed by ring-opening of the epoxy ring. Therefore, this is not an industrially favorable processes for producing 3-methyltetrahydrofuran.

As processes for producing 3-hydroxy-3-methyltetrahydrofuran, the following processes are known: (e) a process of reacting 2-hydroxyethyl-2-methyloxirane with tributyltin methoxide and then thermally decomposing the resultant tin compound to obtain the target compound [see Tetrahedron, 38, pp. 2139–2146 (1982)], (f) a process of decomposing β-tetrahydrofurylmethanol on an alumina catalyst [see Bull. Soc. Chim. Fr., 5–6, Pt 2, pp. 261–266 (1980)], (g) a process of reacting 4-chloro-3-methyl-1,3-butanediol with KCN [see Nippon Kagaku Kaishi, pp. 1021–1025 (1977)], (h) a process of decomposing 4,4-dimethyl-1,3-dioxane [see Meiji Daigaku Kagaku Gijutu Kenkyusho Nempo, 17, p. 22 (1975)].

However, all of the above-mentioned processes have problems. In process (e), an expensive compound must be used to produce 3-hydroxy-3-methyltetrahydrofuran, and selectivity of 3-hydroxy-3-methyltetrahydrofuran is as low as 50%. In process (f), the raw material cannot be easily available, and a high temperature of 300° C., or higher is necessary for the decomposition. In process (g), the main reaction thereof is cyanization and thus 3-hydroxy-3-methyltetrahydrofuran can be obtained only as a by-product. In process (h), 3-hydroxy-3-methyltetrahydrofuran can be obtained in only a little amount as a by-product, and cannot be selectively obtained.

For such reasons, any industrially-established process for producing 3-hydroxy-3-methyltetrahydrofuran has not been known until now.

As processes for producing 3-methyldihydrofuran, in particular, 3-methyl-4,5-dihydrofuran or 3-methyl-2,5-dihydrofuran, the following processes are known: (i) a process of hydroformylating methacrolein diethylacetal, reducing its aldehyde group, cyclizing the resultant alcohol compound, and subjecting eliminating ethanol from the cyclic compound to obtain 3-methyl-4,5-dihydrofuran [see J. Org. Chem., 37, p. 1835 (1972)], (j) a process of isomerizing 3-methyl-3,4-epoxy-1-butene in the presence of a higher tertiary amine and a zinc oxide catalyst to obtain 3-methyl-2,5-dihydrofuran [see WO 91/13882], (k) a process of isomerizing isoprene oxide in the presence of iron acetylacetonate (Fe(acac)$_3$) and hydrogen iodide to obtain 3-methyl-2,5-dihydrofuran [see U.S. Pat. No. 3,932,468], (l) a process of reacting hydroxyacetone with vinyltriphenylphosphonium bromide, and following to cyclization reaction of the resultant to obtain 3-methyl-2,5-dihydrofuran [see J. Org. Chem., 33, p. 583 (1968)].

However, in process (i), methacrolein, which is not stable, must be converted to the acetal, a rhodium catalyst using in the hydroformylation reaction is very expensive, and it needs the number of steps. In process (j), the preparation of the catalyst is difficult. In process (k), it is necessary to use hydrogen iodide which is highly corrosive. In process (l), a large amount of expensive triphenylphosphine is necessary to prepare vinyltriphenylphosphonium bromide, which is used in a mole equivalent to hydroxyacetone. Therefore, these processes are not industrially-profitable processes for producing 3-methyldihydrofuran.

SUMMARY OF THE INVENTION

It is an object of the present invention to provide a process for producing 3-methyltetrahydrofuran with simplicity and industrial-profitability and in a high yield, from a starting material that can easily be obtained.

It is another object of the present invention to provide a process for producing 3-hydroxy-3-methyltetrahydrofuran safely, economically and industrially.

It is another object of the present invention to provide a process for producing 3-methyldihydrofuran with simplicity and industrial-profitability and in a high yield.

Thus, a first aspect of the present invention is a process for producing 3-methyltetrahydrofuran, comprising the steps of reacting 3-methyl-3-buten-1-ol with hydrogen peroxide in the presence of a zeolite to obtain 3-hydroxy-3-methyltetrahydrofuran, and reacting the resultant 3-hydroxy-3-methyltetrahydrofuran with hydrogen in the presence of an acidic substance and a hydrogenation catalyst.

A second aspect of the present invention is a process for producing 3-methyltetrahydrofuran, comprising reacting 3-hydroxy-3-methyltetrahydrofuran with hydrogen in the presence of an acidic substance and a hydrogenation catalyst.

A third aspect of the present invention is a process for producing 3-hydroxy-3-methyltetrahydrofuran, comprising reacting 3-methyl-3-buten-1-ol with hydrogen peroxide in the presence of a zeolite.

A fourth aspect of the present invention is a process for producing 3-methyldihydrofuran, comprising dehydrating 3-hydroxy-3-methyltetrahydrofuran in the presence of an acidic substance.

A fifth aspect of the present invention is a process for producing 3-methyltetrahydrofuran, comprising reacting 3-methyldihydrofuran with hydrogen in the presence of a hydrogenation catalyst.

A sixth aspect of the present invention is a process for producing 3-methyltetrahydrofuran, comprising cyclizing 3-methyl-3-buten-1-ol in the presence of iodine.

A more complete appreciation of the invention and many of the attendant advantages thereof will be readily obtained as the same becomes better understood by reference to the following detailed description.

DETAILED DESCRIPTION OF THE INVENTION

Each step of the producing process of the present invention will be described in detail.

(1) Reacting 3-methyl-3-buten-1-ol with hydrogen peroxide in the presence of zeolite to obtain 3-hydroxy-3-methyltetrahydrofuran 3-methyl-3-buten-1-ol, which is used as a starting material in the present step, can easily be synthesized, for example, by condensing formaldehyde with isobutene under heating [see Angew. Chem. Int. Ed. Engl., 8, p. 556(1969)].

The zeolite acts as a catalyst for the reaction in the present step. Zeolite includes a metallosilicate such as titanosilicate prepared from a tetraalkylorthosilicate, a tetraalkylorthotitanate and a tetraalkylammonium salt as a mold release agent; and zirconosilicate prepared from a tetraalkylorthosilicate, a tetraalkylorthozirconate and a tetraalkylammonium salt as a mold release agent. Among them, titanosilicate is preferred. More preferred is TS-1, which is titanosilicate obtained by hydrothermal synthesis of a mixture of tetraethylorthosilicate $(Si(OEt)_4)$ and tetraethylorthotitanate$(Ti(OEt)_4)$ $(Si(OEt)_4$: $Ti(OEt)_4$=40:1 (molar ratio) at 175° C. in the presence of a catalytic amount of tetrapropylammonium hydroxide $(Pr_4NOH)$. The amount of zeolite to be used is preferably from 0.01 to 100%, and more preferably, from 0.1 to 10% by weight of 3-methyl-3-buten-1-ol. If the amount of zeolite to be used is less than 0.01% by weight, the reaction trends to advance slowly. Amounts of zeolite of more than 100% by weight is not preferred for easy operation and economy.

The concentration of the hydrogen peroxide to be used in the reaction is not particularly limited. If the concentration is high, volume efficiency is improved so that productivity is improved, however, safety decreases. Considering easy operation, safety, economy and the like, it is preferred to use a hydrogen peroxide solution having a concentration of 10–60%, which is commercially available in general. The amount of hydrogen peroxide to be used is , the amount converted to the contained hydrogen peroxide, preferably at a ratio of from 0.5 to 2 moles based on one mole of 3-methyl-3-buten-1-ol.

The reaction can be performed in the presence or absence of a solvent. The solvent that can be used is not especially limited unless the solvent has a influence to the reaction. The solvent may be a solvent that can not be reacted with hydrogen peroxide, examples of which include halogenated hydrocarbons such as dichloromethane, 1,2-dichloroethane, chloroform, carbon tetrachloride and chlorobenzene; aliphatic hydrocarbons such as pentane, hexane, heptane, octane, cyclohexane and cyclooctane; and aromatic hydrocarbons such as benzene, toluene, xylene and mesitylene. In the case of using the solvent, the weight of the solvent to be used is not especially limited. In general, the weight of the solvent to be used is preferably from 0.01 to 100 parts by weight, and more preferably, from 0.1 to 10 parts by weight based on the one part by weight of 3-methyl-3-buten-1-ol from the viewpoint of smooth advance of the reaction, easy operation and volume efficiency.

The reaction temperature is preferably within a range from 40 to 100° C. If the reaction temperature is lower than 40° C., the reaction trends to advance very slowly. On the other hand, if the reaction temperature is higher than 100° C., hydrogen peroxide is decomposed very quickly so that control of the reaction tends to be difficult.

The reaction may be performed under the atmosphere, but is preferably performed under an inert gas such as nitrogen or argon from the viewpoint of safety. Pressure upon the reaction is not especially limited. The reaction may be performed under atmospheric pressure, increased pressure or reduced pressure.

The reaction is preferably performed as follows: for example, 3-methyl-3-buten-1-ol, zeolite and the optional solvent are mixed in the atmosphere of an inert gas such as nitrogen or argon and the temperature of the mixture is set to a given temperature, and subsequently hydrogen peroxide, preferably in an aqueous solution form, is added dropwise to this mixture with stirring.

The thus obtained 3-hydroxy-3-methyltetrahydrofuran can be isolated and purified in the usual manner for isolation and purification of organic compounds. For example, the reaction mixture is filtrated to remove zeolite and subsequently distilled.

(2) Reacting 3-hydroxy-3-methyltetrahydrofuran with hydrogen in the presence of an acidic substance and a hydrogenation catalyst to obtain 3-methyltetrahydrofuran The acidic substance to be used in the present step contributes to a dehydration reaction of 3-hydroxy-3-methyltetrahydrofuran.

Examples of the acidic substances include inorganic acids or salts thereof such as hydrochloric acid, sulfuric acid, phosphoric acid, polyphosphoric acid, sodium hydrogensulfate, potassium hydrogensulfate, sodium dihydrogenphosphate, potassium dihydrogenphosphate, sodium hydrogensulfite and potassium hydrogensulfite; sulfonic acids such as methanesulfonic acid, benzenesulfonic acid and toluenesulfonic acid; carboxylic acids such as acetic acid, propionic acid, benzoic acid and terephthalic acid; heteropolyacids such as phosphotungstic acid, phosphomolybdic acid, silicotungstic acid and silicomolybdic acid; solid acids such as silica, alumina, silica-alumina, titania, silica-titania and niobium oxide; and acidic ion-exchange resins such as sulfonic acid based ion-exchange resin and carboxylic acid based ion-exchange resin. These acidic substances may be used alone, or as a mixture of two or more of them. Any homogeneous acid such as the above-mentioned inorganic acid, salt thereof, sulfonic acid, carboxylic acid and heteropolyacid may be caused to be adsorbed on activated carbon, silica, alumina, zirconia, titania or the like, so that the resultant may be used in the same way as the solid acid. The amount of the acidic substance to be used is not especially limited. In the case of using the homogeneous acid such as the above-mentioned inorganic acid, salt thereof, sulfonic acid, carboxylic acid or heteropolyacid as the acidic substance, in general, the amount to be used thereof is preferably from 0.001 to 50% by mole, and more preferably, from 0.01 to 10% by mole per mole of 3-hydroxy-3-methyltetrahydrofuran from the viewpoint of reaction efficiency and economy. In the case of using the above-mentioned solid acid, the acidic ion-exchange resin, or the homogeneous acid adsorbed on a carrier as the acidic substance, in general, the amount to be used thereof is preferably from 0.01 to 10% by weight of 3-hydroxy-3-methyltetrahydrofuran.

Examples of the hydrogenation catalyst include noble metal oxides such as palladium oxide and platinum oxide; noble metal catalysts such as palladium, ruthenium, rhodium or platinum supported on a carrier such as activated carbon, silica, silica-alumina, silica-titania or an acidic ion-exchange resin; nickel catalysts such as nickel oxide, Raney nickel and nickel diatom earth; and copper catalysts such as Raney copper, copper chromite and copper zinc. These hydrogenation catalysts may be used alone, or as a mixture of two or more of them. The amount of the hydrogenation catalyst to be used is not especially limited. Usually, the amount of the hydrogenation catalyst to be used is preferably from 0.001 to 100%, more preferably from 0.01 to 50%, and most preferably from 0.05 to 10% by weight of 3-hydroxy-3-methyltetrahydrofuran from the viewpoint of easy operation, reactivity and economy.

In the case of using the noble catalyst supported on the acidic substance such as alumina, silica, silica-alumina, silica-titania or acidic ion-exchange resin as the hydrogenation catalyst, the above-mentioned acidic substance may not be used.

The hydrogen pressure is not especially limited. Usually, the hydrogen pressure is preferably from an atmospheric pressure to 20 MPa, more preferably from an atmospheric pressure to 5 MPa, and most preferably from an atomospheric pressure to 2 MPa from the viewpoint of easy operation, safety and smooth advance of the reaction.

The reaction can be performed in the presence or absence of a solvent. The solvent that can be used is not especially limited unless it has a influence to the reaction. Examples thereof include aliphatic hydrocarbons such as pentane, hexane, heptane, octane, nonane, decane, cyclohexane and cyclooctane; aromatic hydrocarbons such as benzene, toluene, xylene, mesitylene; alcohols such as methanol, ethanol, propanol, isopropanol, butanol and octanol: and ethers such as diethyl ether, diisopropyl ether and tetrahydrofuran. In the case of using the solvent, the weight of the solvent to be used is not especially limited. In general, the weight of the solvent to be used is preferably from 0.01 to 100 parts by weight, and more preferably, from 0.1 to 10 parts by weight based on the one part by weight of 3-hydroxy-3-methyltetrahydrofuran from the viewpoint of smooth advance of the reaction, easy operation and volume efficiency. The reaction temperature is preferably within a range from 0 to 200° C., more preferably within a range from 20 to 150° C., and most preferably within a range from 60 to 150° C. from the viewpoint of easy operation, smooth advance of the reaction and safety.

The reaction is preferably performed as follows: for example, into a reaction vessel are charged 3-hydroxy-3-methyltetrahydrofuran, the acidic substance, the hydrogenation catalyst, and the optional solvent, and then the vessel is sealed. Thereafter, the vessel is pressurized with hydrogen, and the mixture is stirred at a given temperature. The reaction may be performed in a batch manner or in a continuous manner.

The thus obtained 3-methyltetrahydrofuran can be isolated and purified in the usual manner for isolation and purification of organic compounds. For example, the reaction mixture is filtrated, the resultant filtrate is optionally washed with water, and subsequently distilled.

(3) Subjecting 3-hydroxy-3-methyltetrahydrofuran to dehydration reaction in the presence of an acidic substance to obtain 3-methyldihydrofuran Examples of the acidic substances to be used include inorganic acids or salts thereof such as hydrochloric acid, sulfuric acid, phosphoric acid, polyphosphoric acid, sodium hydrogensulfate, potassium hydrogensulfate, sodium dihydrogenphosphate, potassium dihydrogenphosphate, sodium hydrogensulfite and potassium hydrogensulfite; sulfonic acids such as methanesulfonic acid, benezenesulfonic acid and toluenesulfonic acid; carboxylic acids such as acetic acid, propionic acid, benzoic acid and terephthalic acid; heteropolyacids such as phosphotungstic acid, phosphomolybdic acid, silicotungstic acid and silicomolybdic acid; solid acids such as silica, alumina, silica-alumina, titania, silica-titania and niobium oxide; and acidic ion-exchange resins such as sulfonic acid based ion-exchange resin and carboxylic acid based ion-exchange resin.

These acidic substances may be used alone, or as a mixture of two or more of them. Any homogeneous acid such as the above-mentioned inorganic acid, salt thereof, sulfonic acid, carboxylic acid and heteropolyacid may be caused to be adsorbed on activated carbon, silica, alumina, zirconia, titania or the like, so that the resultant may be used in the same way as the solid acid. The amount of the acidic substance to be used is not especially limited. In the case of using the homogeneous acid such as the above-mentioned inorganic acid, salt thereof, sulfonic acid, carboxylic acid or heteropolyacid as the acidic substance, in general, the amount to be used thereof is preferably from 0.001 to 50% by mole, and more preferably, from 0.01 to 10% by mole per mole of 3-hydroxy-3-methyltetrahydrofuran from the viewpoint of reaction efficiency and economy. In the case of using the above-mentioned solid acid, the acidic ion-exchange resin, or homogeneous acid adsorbed on activated carbon, silica, alumina or the like as the acidic substance, in general, the amount to be used thereof is preferably from 0.01 to 10% by weight of 3-hydroxy-3-methyltetrahydrofuran.

The reaction can be performed in the presence or absence of a solvent. The solvent that can be used is not especially limited unless it has a influence to the reaction. Examples thereof include aliphatic hydrocarbons such as pentane, hexane, heptane, octane, nonane, decane, cyclohexane and cyclooctane; aromatic hydrocarbons such as benzene, toluene, xylene, mesitylene; alcohols such as methanol, ethanol, propanol, isopropanol, butanol and octanol; and ethers such as diethyl ether, diisopropyl ether and tetrahydrofuran and halogenated hydrocarbons such as dichloromethane, chloroform, carbon tetrachloride, 1,2-dichloroethane and chlorobenzene. In the case of using the solvent, the weight of the solvent to be used is not especially limited. In general the weight of the solvent to be used is preferably from 0.01 to 10 parts by weight, and more preferably from 0.1 to 2 parts by weight based on the one part by weight of 3-hydroxy-3-methyltetrahydrofuran from the viewpoint of smooth advance of the reaction, volume efficiency and economy.

The reaction temperature is preferably within a range from 40 to 200° C., and more preferably within a range from 60–140° C. If the reaction temperature is lower than 40° C., the reaction trends to advance slowly. If the reaction temperature is higher than 200° C., selectivity of 3-methyldihydrofuran tends to decrease because of increasing by-products having high-boiling point derived from 3-methyldihydrofuran.

The reaction can be performed as follows: for example, the acidic substance, 3-hydroxy-3-methyltetrahydrofuran and the optional solvent are mixed and stirred at a given temperature. The reaction may be performed in a batch manner or in a continuous manner. From the viewpoint of stability of a product and productivity, a continuous manner is preferred. In the case that the reaction is performed in a continuous manner, since 3-methyldihydrofuran as the product has a boiling point lower than 3-hydroxy-3-methyltetrahydrofuran as a raw material, it is preferred as a reaction method that 3-hydroxy3-methyltetrahydrofuran is added continuously to the dissolved or suspended solution of the solvent and the acidic substance, which is kept at a given temperature, while stirring, and the resultant product is distilled out simultaneously. In this method, it is preferred to use a solvent having a boiling point higher than 3-hydroxy-3-methyltetrahydrofuran.

The purity of the resultant 3-methyldihydrofuran, that is, 3-methyl-4,5-dihydrofuran or 3-methyl-2,5-dihydrofuran, can be made higher by an usual purifying method such as distillation.

(4) Reacting 3-methyldihydrofuran with hydrogen in the presence of a hydrogenation catalyst to obtain 3-methyltetrahydrofuran 3-methyldihydrofuran that can be used may be, for example, 3-methyl-4,5-dihydrofuran or 3-methyl-2,5-dihydrofuran, or a mixture thereof.

Examples of the hydrogenation catalyst include noble metal oxides such as palladium oxide and platinum oxide; noble metal catalysts such as palladium, ruthenium, rhodium or platinum supported on carrier such as activated carbon, silica, alumina, silica-alumina, silica-titania or an acidic ion-exchange resin; nickel catalysts such as nickel oxide, Raney nickel and nickel diatom earth; and copper catalysts such as Raney copper, copper chromite and copper zinc.

These hydrogenation catalysts may be used alone, or as a mixture of two or more of them. The amount of the hydrogenation catalyst to be used is not especially limited. Usually, the amount of the hydrogenation catalyst to be used is preferably from 0.001 to 100%, more preferably from 0.01 to 50%, and most preferably from 0.05 to 10% by weight of 3-methyldihydrofuran from the viewpoint of easy operation, reactivity and economy.

The hydrogen pressure is not especially limited. Usually, the hydrogen pressure is preferably from an atmospheric pressure to 20 MPa, more preferably from an atmospheric pressure to 5 MPa, and most preferably from an atomospheric pressure to 2 MPa from the viewpoint of easy operation, safety and smooth advance of the reaction.

The reaction can be performed in the presence or absence of a solvent. The solvent that can be used is not especially limited unless it has a influence to the reaction. Examples thereof include aliphatic hydrocarbons such as pentane, hexane, heptane, octane, nonane, decane, cyclohexane and cyclooctane; aromatic hydrocarbons such as benzene, toluene, xylene, mesitylene; alcohols such as methanol, ethanol, propanol, isopropanol, butanol and octanol; and ethers such as diethyl ether, diisopropyl ether and tetrahydrofuran. In the case of using the solvent, the weight of the solvent to be used is not especially limited. In general, the weight of the solvent to be used is preferably from 0.01 to 100 parts by weight, and more preferably, from 0.1 to 10 parts by weight based on the one part by weight of 3-methyldihydrofuran from the viewpoint of smooth advance of the reaction, easy operation and volume efficiency.

The reaction temperature is preferably within a range from 0 to 200° C., more preferably within a range from 20–150° C. and most preferably within a range from 60–150° C. from the viewpoint of easy operation, safety, smooth advance of the reaction.

The reaction can be preferably performed as follows: for example, into a reaction vessel are charged 3-methyldihydrofuran, the hydrogenation catalyst and the optional solvent, and then the vessel is sealed. Thereafter, the reaction vessel is pressurized with hydrogen, and the reactant is stirred at a given temperature. The reaction may be performed in a batch manner or in a continuous manner.

The thus obtained 3-methyltetrahydrofuran can be isolated and purified in the usual manner for isolation and purification of organic compounds. For example, the reaction mixture is filtrated, the resultant filtrate is optionally washed with water, and subsequently distilled.

(5) Cyclizing 3-methyl-3-buten-1-ol in the presence of iodine to obtain 3-methyltetrahydrofuran Commercially available iodine may be used, but purified iodine, for example, purified by sublimation, is preferred. The amount of iodine to be used is not especially limited. The amount of iodine to be used is preferably at a ratio of from 0.001 to 1 mole, and more preferably, at a ratio of from 0.001 to 0.1 mole based on one mole of 3-methyl-3-buten-1-ol from the viewpoint of post-treatment.

The reaction is preferably performed in the presence of a solvent. The solvent that can be used is not especially limited unless the solvent has a influence to the reaction. Examples of the solvent include halogenated hydrocarbons such as dichloromethane, chloroform, 1,2-dichloroethane and carbon tetrachloride; ethers such as diethyl ether, diisopropyl ether, dibutyl ether, tetrahydrofuran, tetrahydropyran, 4-methyltetrahydropyran and 1,4-dioxane; hydrocarbons such as pentane, hexane, heptane, octane, cyclohexane and cyclooctane; and alcohols such as methanol, ethanol, propanol, isopropanol, butanol and tertbutanol. The weight of the solvent to be used is not especially limited. In general, the weight of the solvent to be used is preferably 0.01–100 parts by weight, and more preferably, 0.1–10 parts by weight based on the one part by weight of 3-methyl-3-buten-1-ol.

The reaction may be preferably performed under an inert gas atmosphere. Examples of such an inert gas include helium, nitrogen and argon. These inert gases may be used alone or as a mixture of two or more of them.

The reaction pressure is not especially limited. The reaction may be performed under atmospheric pressure, increased pressure or reduced pressure. Preferably, the reaction may be performed under atmospheric pressure from the viewpoint of reaction devices, facilities and easy operation.

The reaction temperature is not especially limited. Usually, the reaction temperature is preferably within a range from −80 to 200° C., and more preferably, within a range from 0 to 100° C. from the viewpoint of easy operation and safety. If the reaction temperature is lower than −80° C., the reaction trends to advance very slowly. If the reaction temperature is higher than 200° C., the amount of by-products such as isoprene trends to increase.

The reaction is preferably performed as follows: iodine and the solvent are mixed and the temperature of the mixture is set to a given temperature. Then, 3-methyl-3-buten-ol is added dropwise to this solution with stirring.

The thus obtained 3-methyltetrahydrofuran can be isolated and purified in the usual manner for isolation and purification of organic compounds. For example sodium thiosulfate is added to the reaction solution to remove iodine, the solvent is removed if necessary, and subsequently distillation is performed. Since water is not produced by a by-product in the present step (5), 3-methyltetrahydrofuran having a high purity can be obtained by only distillation.

According to the process of the present invention, it is possible to produce 3-hydroxy3-methyltetrahydrofuran, 3-methyldihydrofuran and 3-methyltetrahydrofuran with ease and industrial profitability and in a high yield from 3-methyl-3-buten-1-ol as a raw material, which is easily available.

EXAMPLES

Having generally described this invention, a further understanding can be obtained by reference to certain specific examples which are provided herein for purposes of illustration only and are not intended to be limiting unless otherwise specified.

Example 1

Into a 100 ml three-necked flask equipped with a mechanical stirrer, a reflux condenser, a thermometer and a dropping funnel were charged 30 g (0.35 mol) of 3-methyl3-buten-1-ol and 0.3 g of TS-1 as a catalyst, and then the system was replaced by nitrogen. The temperature of the mixture was raised to 60° C. while stirring the mixture so that the TS-1 would be homogeneously dispersed.

Thereafter, 40 g (0.35 mol) of aqueous 30% hydrogen peroxide was added dropwise thereto over 2 hours. After the addition, the reaction solution was stirred at the same temperature, and advance of the reaction was traced by gas chromatography analysis (column: CBP-10, column length: 50 m (GL Sciences, Inc), column temperature: 70° C. (constant)). After 2 hours, disappearance of hydrogen peroxide was confirmed by using paper for detecting hydrogen peroxide. TS-1 was separated by filtration. To the filtrate was added 0.1 g of cobalt acetate, and then the mixture was distilled to give 35.1 g of a product. The product contained 32.0 g of 3-hydroxy-3-methyltetrahydrofuran (conversion of 3-methyl-3-buten-1-ol: 97.3%, selectivity of 3-hydroxy-3-methyltetrahydrofuran: 92.2%).

Example 2

In Example 1, any solvent was not used. The same manner as in Example 1 was performed except that 30 g of 1,2-dichloroethane was added as a solvent and further the reaction solution was stirred with a magnetic stirrer using a stirring tip instead of the mechanical stirrer, so as to give 33.7 g of a product. The product contained 31.5 g of 3-hydroxy-3-methyltetrahydrofuran (conversion of 3-methyl-3-buten-1-ol: 95.1%, selectivity of 3-hydroxy-3-methyltetrahydrofuran: 93.1%).

Example 3

The same manner as in Example 2 was performed except that 30 g of toluene was used instead of 30 g of 1,2-dichloroethane, so as to give 31.3 g of a product. The product contained 29.0 g of 3-hydroxy-3-methyltetrahydrofuran (conversion of 3-methyl-3-buten-1-ol: 91.1%, selectivity of 3-hydroxy-3-methyltetrahydrofuran: 89.4%).

Example 4

Into a 100 ml autoclave (Hastelloy C) equipped with an electromagnetic stirring device, a pressure gauge, a needle valve, a gas introducing opening and a sampling opening were charged 20 g of 3-hydroxy-3-methyltetrahydrofuran, 0.05 g of p-toluenesulfonic acid, 20 g of toluene and 0.2 g of 5% palladium-carbon (E106NN, Degussa AG), and then the autoclave was sealed. The air inside the autoclave was replaced by nitrogen, and then the nitrogen was replaced by hydrogen. Next, the pressure inside the autoclave was increased to 0.5 MPa by hydrogen. The temperature in the system was raised to 100° C., and the reaction was performed with stirring for 5 hours. The pressure inside the reactor was kept at 0.5 MPa by supplying hydrogen as consumed in the reaction. After the reaction, the mixture was cooled to room temperature, and then the inside of the system was replaced by nitrogen. The mixture was taken out, a portion of this mixture was analyzed by gas chromatography(column: PEG-HT, column length: 3 m, column diameter: 4 mm; analysis conditions: injection temperature: 220° C., detector temperature: 240° C., column temperature: 70° C. (constant), and carrier gas: helium 40 ml/min., $H_2$ 50 kPa, and air 50 kPa) to find that conversion of 3-hydroxy-3-methyltetrahydrofuran was 98.5% and selectivity of 3-methyltetrahydrofuran was 98%. The resultant reaction solution was distilled under atomospheric pressure to obtain 17.1 g of 3-methyltetrahydrofuran (purity: 98.9%).

Example 5

The same procedures as in Example 4 were performed except that 0.25 g of p-toluenesulfonic acid was used instead of 0.05 g thereof, 0.1 g of Raney nickel (BK111/w, Degussa AG) was used instead of 0.2 g of 5% palladium-carbon, and reaction temperature was set to 120° C. The resultant reaction mixture was analyzed by gas chromatography under the same analysis conditions as in Example 4 to find that conversion of 3-hydroxy-3-methyltetrahydrofuran was 98%, and selectivity of 3-methyltetrahydrofuran was 97.5%.

Example 6

The same procedures as in Example 4 were performed except that 0.25 g of p-toluenesulfonic acid was used instead of 0.05 g thereof, 0.5 g of 1% palladium on acidic ion-exchange resin (N.E. Chemcat Corp.) was used instead of 0.2 g of 5% palladium-carbon, reaction temperature was set to 80° C., and reaction time was set to 12 hours. The resultant reaction mixture was analyzed by gas chromatography under the same analysis conditions as in Example 4 to find that conversion of 3-hydroxy-3-methyltetrahydrofuran was 96%, and selectivity of 3-methyltetrahydrofuran was 95.5%.

Example 7

Into a 200 ml three-necked flask equipped with a thermometer, a reflux condenser and a magnetic stirrer were charged 50 g (0.48 mol) of 3-hydroxy-3-methyltetrahydrofuran, 50 g of mesitylene and 0.1 g of acidic ion-exchange resin (AMBERLYST, Organo Corp.). The temperature of the mixture was raised to 120° C., and the mixture was stirred for 3 hours while the resultant product having a low boiling point was distilled out. The amount of the distillate was 54.2 g. The distillate was analyzed by gas chromatography(column: G-300, 50 m (Chemicals Inspection & Testing Institute, Japan), analysis conditions: injection temperature: 240° C., detector temperature: 220° C., column temperature: 70° C. (constant), and carrier gas: helium 40 ml/min., $H_2$ 50 kPa, and air 50 kPa) to find that 38.3 g of 3-methyldihydrofurans were contained in the distillate (yield: 95.0%, 3-methyl-2,5-dihydrofuran:3-methyl-4,5-dihydrofuran=89:11).

Example 8

Into a 100 ml three-necked flask equipped with a thermometer, a reflux condenser and a magnetic stirrer were charged 20 g (0.19 mol) of 3-hydroxy-3-methyltetrahydrofuran, 20 g of mesitylene and 0.01 g of potassium hydrogensulfate. The temperature of the mixture was raised to 120° C., and the mixture was stirred for 4.2 hours while the resultant product having a low boiling point was distilled out. The amount of the distillate was 22.1 g. The distillate was analyzed by gas chromatography under the same conditions as in Example 7 to find that 15.0 g of 3-methyldihydrofurans were contained in the distillate (yield: 92.8%, 3-methyl-2,5-dihydrofuran:3-methyl-4,5-dihydrofuran=90:10).

Example 9

Into a 100 ml three-necked flask equipped with a thermometer, a reflux condenser and a magnetic stirrer were charged 20 g (0.19 mol) of 3-hydroxy-3-methyltetrahydrofuran, 20 g of decane and 0.01 g of sulfuric acid. The temperature of the mixture was raised to 130° C., and the mixture was stirred for 1.2 hours while the resultant product having a low boiling point was distilled out. The amount of the distillate was 24.3 g. The distillate was analyzed by gas chromatography under the same conditions as in Example 7 to find that 14.2 g of 3-methyldihydrofurans were contained in the distillate (yield: 88.8%, 3-methyl-2,5-dihydrofuran:3-methyl-4,5-dihydrofuran=87:13).

Example 10

Into a 100 ml autoclave (Hastelloy C) equipped with an electromagnetic stirring device, a pressure gauge, a needle valve, a gas introducing opening and a sampling opening were charged 15 g of 3-methyldihydrofurans (3-methyl-2,5-dihydrofuran:3-methyl-4,5-dihydrofuran=90:10) obtained in Example 8, 15 g of isopropanol, 0.15 g of 5% palladium-carbon (5%E106NN/W, Degussa AG), and then the autoclave was sealed. The air inside the autoclave was replaced by nitrogen, and then the nitrogen was replaced by hydrogen. Next, the pressure inside the autoclave was increased to 1 MPa by hydrogen. The temperature in the system was raised to 80° C., and the reaction was performed with stirring for 6 hours. The pressure inside the reactor was kept at 1 MPa by supplying hydrogen as consumed in the reaction. After the reaction, the mixture was cooled to room temperature, and then the inside of the system was replaced by nitrogen. The mixture was taken out, a portion of the mixture was analyzed by gas chromatography (column: PEG-HT, column length: 3 m, column diameter: 4 mm; analysis conditions: injection temperature: 220° C., detector temperature: 240° C., column temperature: 70° C. (constant), and carrier gas: helium 40 ml/min., $H_2$ 50 kPa, and air 50 kPa) to find that conversion of 3-methyldihydrofuran was 100% and selectivity of 3-methyltetrahydrofuran was 97.2%. The mixture was distilled under atomspheric pressure to obtain 13.2 g of 3-methyltetrahydrofuran (purity: 99.8%).

Example 11

Into a 100 ml three-necked flask equipped with a thermometer, a dropping funnel and a dimroth condenser were charged 20 ml of dehydrated dichloromethane and 0.25 g (1 mmol) of iodine, and then the system was replaced by nitrogen. To this mixture solution was added dropwise 17.2 g (0.2 mol) of 3-methyl-3-buten-1-ol at 27° C. over 1 hour. After the addition. the reaction solution was stirred at 27° C., and advance of the reaction was traced by gas chromatography (column: PEG-HT, column length: 3 m, column diameter: 4 mm, injection temperature: 210° C., and column temperature: 70° C. (constant)). After 8 hours, conversion of 3-methyl-3-buten-1-ol was 98.2%, and selectivity of 3-methyltetrahydrofuran was 96.2%. To this reaction solution was added 1.4 g of sodium thiosulfate, and then the mixture was distilled to obtain 14.9 g (recovery ratio: 92%) of 3-methyltetrahydrofuran.

Example 12

Reaction was conducted in the same way as in Example 11 except that 20 ml of hexane was used instead of 20 ml of dichloromethane. After 12 hours, conversion of 3-methyl-3-buten-1-ol was 89.4%, and selectivity of 3-methyltetrahydrofuran was 89.9%.

Example 13

Reaction was conducted in the same way as in Example 11 except that 20 ml of carbon tetrachloride was used instead of 20 ml of dichloromethane. After 15 hours, conversion of 3-methyl-3-buten-1-ol was 93.3%, and selectivity of 3-methyltetrahydrofuran was 92.2%.

Example 14

Reaction was conducted in the same way as in Example 11 except that the used amount of iodine was changed from 0.25 g (1 mmol) to 2.5 g (10 mmol). After 30 minutes, conversion of 3-methyl-3-buten-1-ol was 99.3%, and selectivity of 3-methyltetrahydrofuran was 97.2%.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Serial No. 142631/1999, filed May 24, 1999; Japanese Patent Application Serial No. 268274/1999, filed Sep. 22, 1999; Japanese Patent Application Serial No. 346141/1999, filed Dec. 6, 1999; and Japanese Patent Application Serial No. 347467/1999, filed Dec. 7, 1999, each incorporated herein by reference in its entirety.

What is claimed is:

1. A process for producing 3-methyltetrahydrofuran, comprising:
    reacting 3-methyl-3-buten-1-ol with hydrogen peroxide in the presence of a zeolite to produce 3-hydroxy-3-methyltetrahydrofuran, and
    reacting the 3-hydroxy-3-methyltetrahydrofuran with hydrogen in the presence of an acidic substance and a hydrogenation catalyst.

2. The process of claim 1, wherein the zeolite is selected from titanosilicate and zirconosilicate.

3. The process of claim 1, wherein the amount of hydrogen peroxide is at a ratio of from 0.5 to 2 moles based on one mole of 3-methyl-3-buten-1-ol.

4. The process of claim 1, wherein the acidic substance is selected from the group consisting of an inorganic acid or salt thereof, a sulfonic acid, a carboxylic acid, a heteropolyacid, a solid acid, an acidic ion-exchange resin, and mixtures thereof.

5. The process of claim 1, wherein the hydrogenation catalyst is selected from the group consisting of a noble metal oxide, a noble metal catalyst supported on a carrier, nickel catalyst, copper catalyst, and mixtures thereof.

6. The process of claim 1, wherein the hydrogen pressure is from an atomospheric pressure to 20 MPa.

7. A process for producing 3-methyltetrahydrofuran, comprising:
reacting 3-hydroxy-3-methyltetrahydrofuran with hydrogen in the presence of an acidic substance and a hydrogenation catalyst.

8. The process of claim 7, wherein the acidic substance is selected from the group consisting of an inorganic acid or salt thereof, a sulfonic acid, a carboxylic acid, a heteropolyacid, a solid acid, an acidic ion-exchange resin, and mixtures thereof.

9. The process of claim 7, wherein the hydrogenation catalyst is selected from the group consisting of a noble metal oxide, a noble metal catalyst supported on a carrier, nickel catalyst, copper catalyst, and mixtures thereof.

10. The process of claim 7, wherein the hydrogen pressure is within a range from an atmospheric pressure to 20 MPa.

11. The process of claim 7, wherein the temperature is within a range from 0 to 200° C.

12. A process for producing 3-hydroxy-3-methyltetrahydrofuran, comprising:
reacting 3-methyl-3-buten-1-ol with hydrogen peroxide in the presence of a zeolite.

13. The process of claim 12, wherein the zeolite is a titanosilicate or zirconosilicate.

14. The process of claim 12, wherein the amount of hydrogen peroxide is at a ratio of from 0.5 to 2 moles based on one mole of 3-methyl-3-buten-1-ol.

15. The process of claim 12, wherein the temperature is within a range from 40 to 100° C.

16. A process for producing 3-methyldihydrofuran, comprising:
dehydrating 3-hydroxy-3-methyltetrahydrofuran in the presence of an acidic substance.

17. The process of claim 16, wherein the acidic substance is selected from the group consisting of an inorganic acid or salt thereof, a sulfonic acid, a carboxylic acid, a heteropolyacid, a solid acid, an acidic ion-exchange resin, and mixtures thereof.

18. The process of claim 16, wherein the temperature is within a range from 40 to 200° C.

19. A process for producing 3-methyltetrahydrofuran, comprising:
reacting 3-methyldihydrofuran with hydrogen in the presence of a hydrogenation catalyst.

20. The process of claim 19, wherein the hydrogenation catalyst is selected from the group consisting of a noble metal oxide, a noble metal catalyst supported on a carrier, nickel catalyst, copper catalyst, and mixtures thereof.

21. The process of claim 19, wherein the hydrogen pressure is within a range from an atomospheric pressure to 20 MPa.

22. The process of claim 19, wherein the temperature is within a range from 0 to 200° C.

23. A process for producing 3-methyltetrahydrofuran, comprising:
cyclizing 3-methyl-3-buten-1-ol in the presence of iodine.

24. The process of claim 23, wherein the amount of iodine is at a ratio of from 0.001 to 1 mole based on one mole of 3-methyl-3-buten-1-ol.

25. The process of claim 23, wherein the temperature is within a range from −80 to 200° C.

* * * * *